US005707353A

United States Patent [19]

Mazer et al.

[11] Patent Number: 5,707,353

[45] Date of Patent: Jan. 13, 1998

[54] ORAL ADMINISTRATION OF BENEFICIAL AGENTS

[75] Inventors: Terrence Bruce Mazer, Reynoldsburg; Joseph Edward Walton, Westerville; Ronita Kay Geckle, Columbus; Carl Joseph Piontek, Powell, all of Ohio

[73] Assignee: Abbott Laboratories, Abbott Park, Ill.

[21] Appl. No.: 576,728

[22] Filed: Dec. 21, 1995

[51] Int. Cl.⁶ .................... A61M 37/00

[52] U.S. Cl. .................... 604/83; 604/82; 604/78

[58] Field of Search .................... 604/82, 83, 84, 604/85, 48, 890.1, 77, 78, 79, 80; 239/33; 424/473; 606/234, 235, 236

[56] References Cited

U.S. PATENT DOCUMENTS

| | | | |
|---|---|---|---|
| 3,463,361 | 8/1969 | Cook et al. | 222/144.5 |
| 4,994,031 | 2/1991 | Theeuwes | 604/85 |
| 5,078,734 | 1/1992 | Noble | 606/234 |
| 5,085,335 | 2/1992 | Carbaugh | 220/709 |
| 5,156,335 | 10/1992 | Smith et al. | 239/33 |
| 5,249,702 | 10/1993 | Topp et al. | 604/85 |
| 5,310,555 | 5/1994 | Zimmer | 424/438 |
| 5,439,678 | 8/1995 | Dobrogosz et al. | 424/93.45 |
| 5,487,750 | 1/1996 | Burchett et al. | 606/236 |
| 5,509,605 | 4/1996 | Cripe | 239/33 |
| 5,531,682 | 7/1996 | Mazer et al. | 604/85 |
| 5,531,734 | 7/1996 | Geckle et al. | 604/85 |
| 5,533,973 | 7/1996 | Piontek et al. | 604/85 |
| 5,542,922 | 8/1996 | Petterson et al. | 606/236 |

*Primary Examiner*—Michael Buiz
*Assistant Examiner*—Patrick W. Rasche
*Attorney, Agent, or Firm*—Brian R. Woodworth

[57] ABSTRACT

Apparatus for adding a beneficial agent to a liquid for drinking during oral administration includes a support structure extending transversely across an imperforate walled zone such as the upper end or neck of a bottle or vessel, or of a funnel-like adapter attached to the top of the vessel, with a retention pocket with liquid penetrable walls held by the support structure and comprising at least one beneficial agent secured therein whereby the beneficial agent is taken up in the liquid for drinking during or just prior to oral administration. The beneficial agent may be in either or both of controlled release dosage form or non-controlled release dosage form and may be one or more of nutrients, medicaments, probiotics, electrolytes, rehydration solutions and diagnostic agents, to which a flavoring agent may be added. In the novel method a support structure with a retention pocket comprising at least one beneficial agent is provided in a bottle or vessel with the support structure extending transversely of the neck or top of the bottle or vessel or a drinking tube extending thereinto. The bottle or vessel is provided with a liquid for drinking selected from a liquid nutritional product, a beverage or water and the liquid is contacted with the beneficial agent during or just before oral administration thereof.

12 Claims, 16 Drawing Sheets

ORAL ADMINISTRATION OF BENEFICIAL AGENTS

FIELD OF THE INVENTION

The invention relates to an apparatus and method for administering medications, supplemental nutrients or other beneficial agents in solution or dispersed form while feeding or supplying a person of any age, but more generally an infant or elderly person, a liquid nutritional product or other suitable orally ingested liquid having a viscosity of from 1 to about 300 centipoises by adding the beneficial agent to the liquid being ingested during or just preceding oral intake.

BACKGROUND OF THE INVENTION

Administering medication or supplemental nutrients orally to an infant often presents problems, not only with the physical aspects of swallowing dosage forms such as tablets, but also, in a typical case of the older infant, with apprehensive refusal to ingest anything "good for you". It is not practical or safe to administer tablets, then, to the very young. It is also often desirable to be able to add supplemental nutrients or medicaments or other beneficial agents very simply to the liquid diet of an infant or an older adult on a made-to-order basis where the quantities do not justify commercially prepared products.

U.S. Pat. No. 5,383,906 describes and claims a device for dispensing a medication into an infant formula in a nursing bottle specially equipped with a syringe-holding sleeve axially disposed within the bottle, the syringe delivering medication through the sleeve within the bottle and adjacent the attached nipple during nursing upon the care giver pressing the plunger of the syringe. This approach has the disadvantage of requiring the use of prepared liquid form medications drawn from bottles or vials as well as the use of sterile syringes and their handling.

SUMMARY OF THE INVENTION

The apparatus of the invention is used for adding, on an inline basis at the time of administration, a useful amount of at least one beneficial agent, selected from the group consisting of nutrients, medicaments, probiotics, electrolytes, rehydration solutions and diagnostic agents, to a liquid for drinking during the oral ingestion thereof, to modify beneficially the liquid for drinking. The liquid for drinking will ordinarily be selected from the group consisting of a liquid nutritional product, a beverage and water. The apparatus and method may also be used to add such beneficial agents just prior to administration of the liquid for drinking. Flavoring agents may also be administered along with any of the beneficial agents.

The apparatus comprises a support structure adapted to extend transversely of an imperforate walled zone through which a liquid for drinking passes during oral ingestion thereof and further comprises at least one beneficial agent secured by the support structure. The support structure includes a pocket with porous or perforated liquid penetrable walls in which the at least one beneficial agent is secured while the liquid for drinking courses thereover or while it is immersed in the liquid for drinking, and the at least one beneficial agent is in a form and amount adapted to be taken up in the liquid for drinking during the ingestion of a preselected quantity thereof or during immersion in the preselected quantity just prior to its administration.

The imperforate walled zone may take the form of the neck portion of a nursing bottle, the neck of a drinking bottle for athletes of any age, a funnel-shaped adapter with projecting spike for piercing and drinking from a closed container such as a soft drink can, the spout of an adapter that slides over and surrounds the top of the sidewall of an open-topped vessel, such as a child's drinking cup adapter, or a drinking straw-shaped tube, optionally with an enlarged section that parts transversely for installation of the support structure with the pocket for holding beneficial agent.

The invention further contemplates a method for modifying a quantity of liquid for drinking during or just prior to oral administration thereof, the liquid for drinking being selected from the group consisting of a liquid nutritional product, a beverage and water, the method comprising the steps of providing a preselected quantity of liquid for drinking to be administered; providing an imperforate walled zone through which the liquid for drinking passes in the process of being administered orally, the imperforate walled zone having a support structure extending transversely thereof and the support structure comprising a useful amount of at least one beneficial agent, the beneficial agent being selected from the group consisting of nutrients, medicaments, probiotics, soluble fibers, electrolytes, rehydration solutions and diagnostic agents, the support structure having a retention pocket with liquid penetrable walls in which the at least one beneficial agent is secured while the liquid for drinking courses thereover and through the walls of the retention pocket during oral administration of the liquid for drinking or while the liquid for drinking enters through the walls of the retention pocket while the retention pocket is immersed in the liquid for drinking just prior to oral administration; and administering orally the preselected quantity of the liquid for drinking, each at least one beneficial agent secured by the transversely extending structure being substantially taken up in the preselected quantity of liquid for drinking during or just prior to the oral administration thereof.

DETAILED DESCRIPTION OF THE INVENTION

Figure 1A:
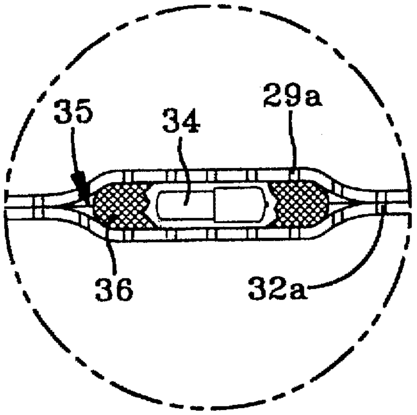
FIG. 1A is a greatly enlarged fragmentary view, partly broken away and in section, of the support structure and retention pocket shown in FIG. 1 and the beneficial agent dosage form held within the retention pocket.

The apparatus and method of the invention are advantageously and simply used to administer medication to individuals of any age, infants, children and adults, who have difficulty swallowing tablets or to supplement the liquid diets of individuals who must rely entirely or partly on a liquid diet, but who are capable of swallowing a liquid orally administered. Oral administration is carried out as by feeding an infant from a nursing bottle equipped with a nipple, or supplying a quantity of liquid from a can or other container equipped with a tube or spout for drinking, or from a cup or tumbler using a straw-like drinking tube, to conscious individuals of any age capable of closing their lips around a tube or spout and sucking on it sufficiently to draw out liquid and orally ingesting, i.e., swallowing, the emerging liquid.

The apparatus of the invention is a support structure that extends transversely of an imperforate walled zone and is provided with a retention pocket in which is secured one or more beneficial agents. The upper end or neck of a nursing bottle is such an imperforate walled zone, as is the neck or spout of any of a drinking bottle, or a section of a drinking tube or straw, or the spout of a funnel-like adapter for attaching to and drinking from cups and glasses or from a can like a soft drink can.

The retention pocket of the support structure may hold one or more beneficial agents in the form of one or more of any of controlled release dosage forms or devices or coated granulations or capsules containing coated or uncoated granules or simply uncoated granules or compressed tablets of one or more beneficial agents. Controlled release dosage forms generally are of advantage when it is desired to provide a beneficial agent at a uniform rate over a time interval of 20 minutes or more, while the compressed tablet or granule dosage form is simple to use and is usually less costly, though a retention pocket is then preferred that will retain particles larger than about 60 to 80 mesh, U.S. Sieve Series, of disintegrating granules or tablets until the particles dissolve or substantially disperse.

It is essential that the retention pocket permit sufficient access, as by flow or immersion, of the liquid for drinking to facilitate up-take of the one or more beneficial agents, and wherein all or most of the liquid for drinking must flow through the retention pocket, the walls thereof must permit adequate flow of the liquid for drinking for the individual receiving the liquid. Thus, the walls of the retention pocket must be perforated or mesh-like or screen-like or highly porous, or the retention pocket must be skeletal in nature, to be sufficiently liquid penetrable to afford adequate liquid flow through the structure and through the nipple, spout or drinking tube during oral administration of the liquid for drinking.

A portion of the support structure may also serve as a skeletal retention pocket or the support structure may hold a retention pocket formed of a screen-like material or a highly porous tea-bag like material, or the support structure may be formed of, for example, opposed perforated plates that are joined at their edges to an imperforate wall to form a retention pocket.

Screen-like walls should be about 20 to 80 mesh, U.S. Sieve Series, to afford suitable liquid flow through the retention pocket, a coarser screen being more suitable for higher viscosity liquids for drinking and the finer screen being usable for liquids of lower viscosity.

The purpose of the retention pocket is simply to position the solid form or carrier of the one or more beneficial agents in the liquid for drinking so that uptake into the liquid for drinking is achieved during immersion just prior to or by flowing contact during the course of the ingestion of most of a given quantity of liquid for drinking in the vessel, cup, glass or can in which the liquid is carried to the intended recipient. If the beneficial agent(s) is in particulate form or disintegrates into particulate form on contact with the liquid for drinking, it is desirable and may be essential to prevent solid particles greater than that passing about a 20 to 80 mesh screen from escaping the retention pocket. Therefore, the support structure to be utilized should be selected with a view to the nature of the beneficial agent being administered to have a suitable retention pocket. If the beneficial agent is supplied from a controlled release dosage form such as an osmotic device, the retention pocket need be little more than a skeletal structure which retains the osmotic device in the liquid for drinking or as the liquid for drinking flows over it.

A beneficial agent not in controlled release dosage form, whether tabletted or agglomerated or loose particulate, also may be placed in measured amount in a retention pocket having walls formed of sufficiently fine screen or in a porous carrier such as one or more fibrous packets of the sort shown, and the packet or packets positioned in a retention pocket of the support structure of the invention. A beneficial agent in a coated tablet or in a capsule that protects the beneficial agent from decomposition or change when in contact with moisture or atmospheric gases may advantageously be administered using the present apparatus and method that does not require the use of previously prepared and stored liquid compositions, provided the beneficial agent is released from the tablet or capsule into a liquid for drinking during the course of oral ingestion of a typical amount of the liquid for drinking, generally eight ounces or less.

The support structure does not need necessarily to support the retention pocket in the neck or spout, but, if desired, may support the retention pocket well down in a bottle or can where the beneficial agent will be immersed in the liquid for drinking and taken up, ordinarily shortly before the liquid for drinking is administered to the individual, especially if any beneficial agent is not quite rapidly taken up.

A liquid nutritional product is to be understood to be a balanced or special liquid nutritional liquid diet.

The term just prior to the time of oral ingestion refers to a time interval of up to about four hours and preferably up to about two hours or less before oral administration.

One or more flavoring agents may be added with the at least one beneficial agent to mask or modify an undesired flavor.

The term "form and amount of at least one beneficial agent to be taken up readily" means in a form and amount that is dissolved or dispersed in the medium of the liquid for drinking during the time interval in which the liquid for drinking is in contact with the at least one beneficial agent during the course of ingestion of a preselected quantity of the liquid for drinking or during immersion therein just prior to ingestion.

Figure 1:
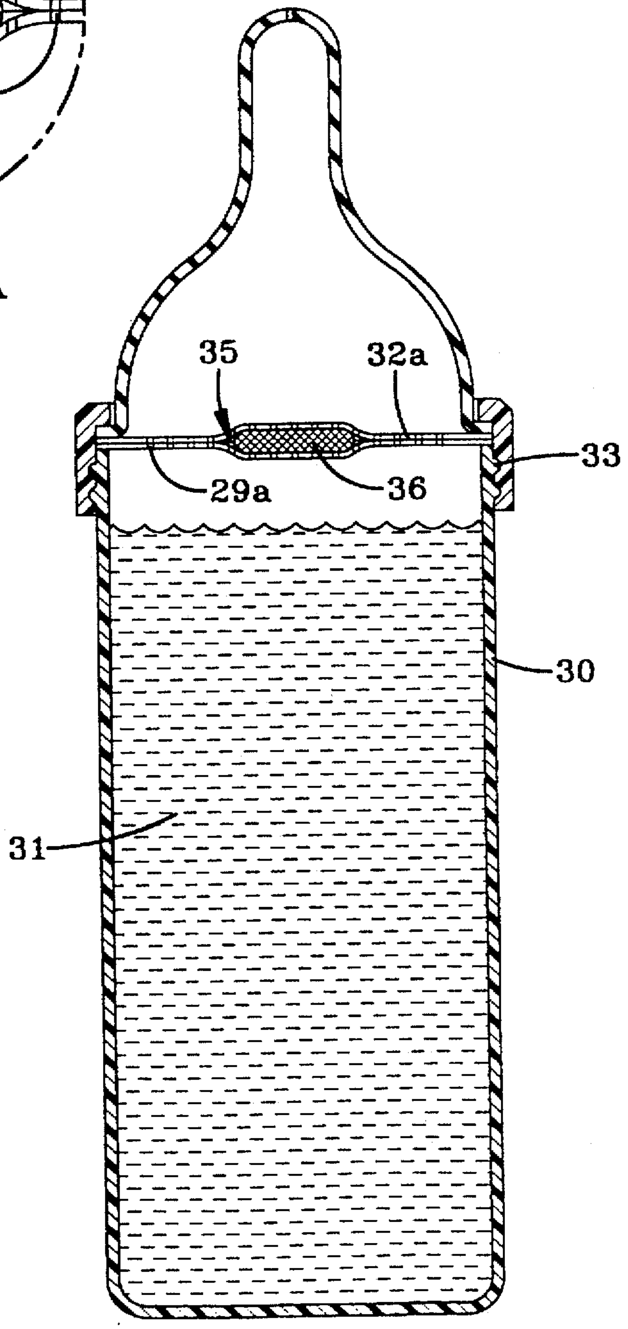
FIG. 1 is a view in section of a nursing bottle containing a liquid for drinking and with apparatus according to the invention extending transversely of the neck portion of the bottle and comprising a quantity of beneficial agent in controlled release or protected form secured in a retention pocket in the transversely extending support structure.

Referring now to FIG. 1 there is seen a view in section of a nursing bottle 30 containing a liquid for drinking 31, such as an infant formula, fruit juice or water, and with the support structure of the invention 32*a* extending transversely of the neck or top portion 33 of the nursing bottle 30 and comprising a quantity of at least one beneficial agent 34 in controlled release or protected form secured in a retention pocket indicated generally by the numeral 35 in the transversely extending structure 32*a*, the retention pocket having screen-like walls 36 and the support structure having perforations 29*a* formed therethrough. The support structure 32*a* may also be skeletal, if desired.

Figure 2A:
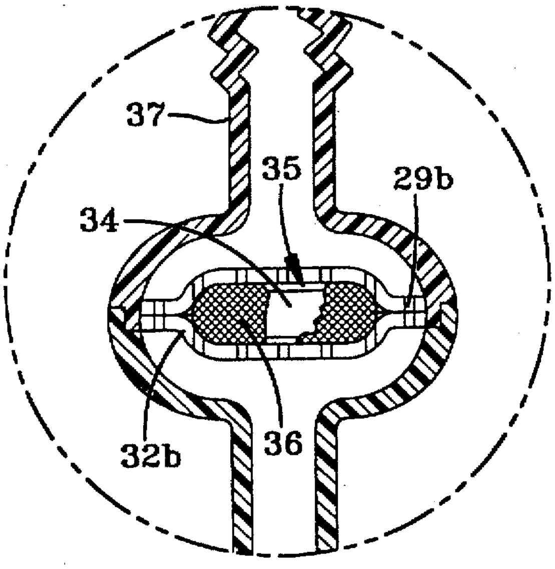
FIG. 2A is a greatly enlarged fragmentary view, partly broken away and in section, of the support structure and retention pocket shown in FIG. 2 and the beneficial agent dosage form held within the retention pocket.
Figure 2:
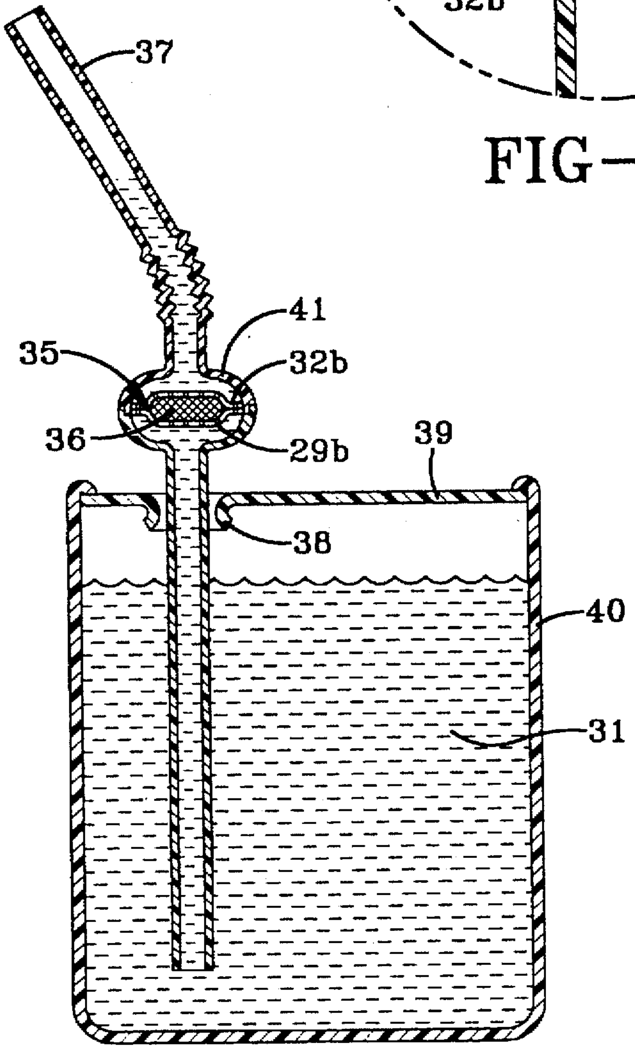
FIG. 2 is a view in section of a covered cup or can of liquid for drinking with a drinking straw-shaped tube extending through an opening in the cover and into the liquid, the tube having an enlarged section in which is transversely mounted the support structure of the invention with a retention pocket in which is secured a quantity of beneficial agent in controlled release or protected form.

As seen in section in FIG. 2, the apparatus of the invention may take the form of a drinking straw-shaped tube 37 extending through an opening 38 in the cover 39 of a covered cup or can 40 of liquid for drinking 31 and into the liquid, the tube 37 having an enlarged section 41 in which is transversely mounted the support structure 32*b* of the invention with a retention pocket indicated generally by the numeral 35 in which is secured a quantity of at least one beneficial agent in controlled release or protected form, the retention pocket having screen-like walls 36 and the support structure having perforations 29*b* formed therethrough. The support structure 32*a* may also be skeletal, if desired.

Figure 3A:
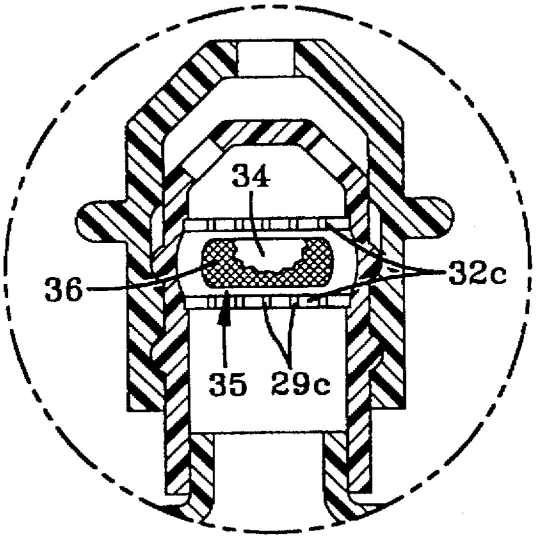
FIG. 3A is a greatly enlarged fragmentary view, partly broken away and in section, of the support structure and retention pocket shown in FIG. 3 and the beneficial agent dosage form held within the retention pocket.
Figure 3:
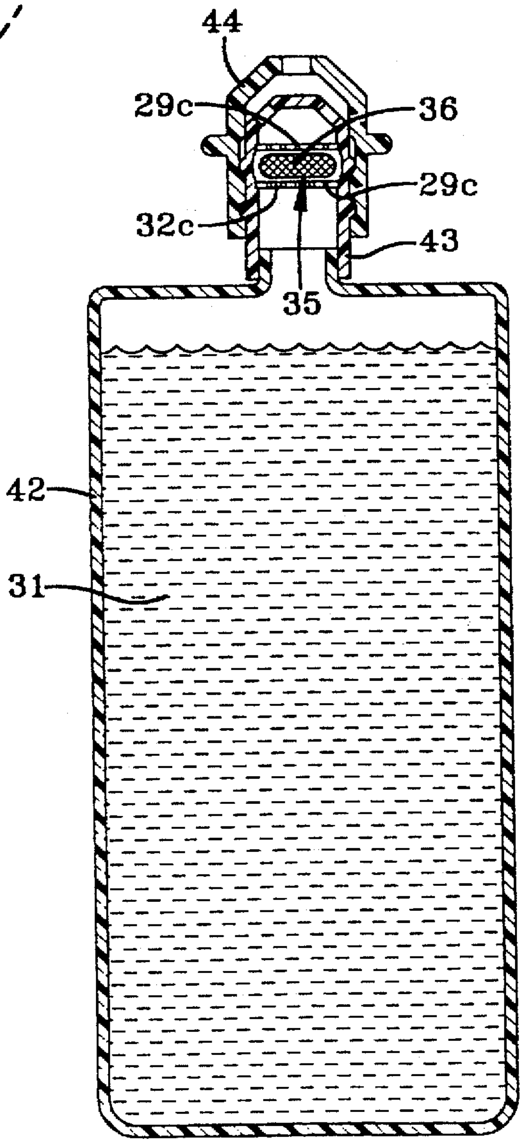
FIG. 3 is a view in section of a drinking bottle with a spout or neck for drinking from the bottle directly and with a reclosable cap, the bottle containing liquid for drinking and being equipped with the structure of the invention extending transversely of the neck portion and comprising a quantity of beneficial agent in controlled release or protected form secured in a retention pocket in the transversely extending structure.

Another application of the apparatus of the invention is shown in FIG. 3 in which there is seen a view in section of a drinking bottle 42, such as that carried by many young athletes with a spout or neck 43 for drinking from the bottle 42 directly and with a reclosable opening structure or cap 44, the bottle 42 containing liquid for drinking 31 and being equipped with the structure 32*c* of the invention extending transversely of the neck portion 43 and comprising a quantity of at least one beneficial agent 34 in controlled release or protected form secured in a retention pocket 35 in the transversely extending structure, the retention pocket 35 having screen-like walls 36 and the support structure having perforations 29*c* formed therethrough. The support structure 32*a* may also be skeletal, if desired.

Figure 4A:
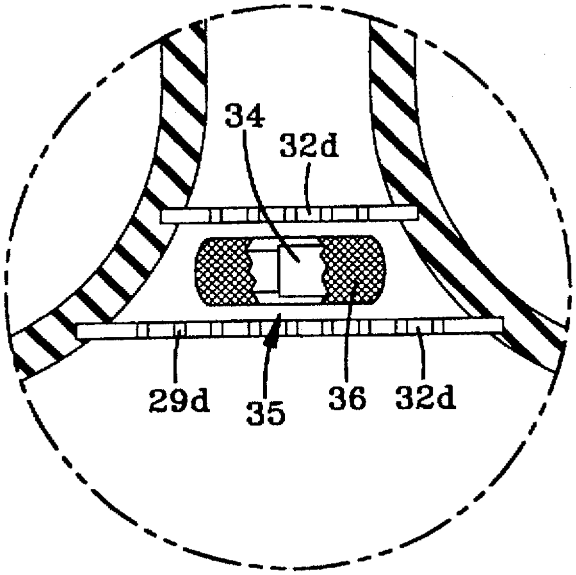
FIG. 4A is a greatly enlarged fragmentary view, partly broken away and in section, of the support structure and retention pocket shown in FIG. 4 and the beneficial agent dosage form held within the retention pocket.
Figure 4:
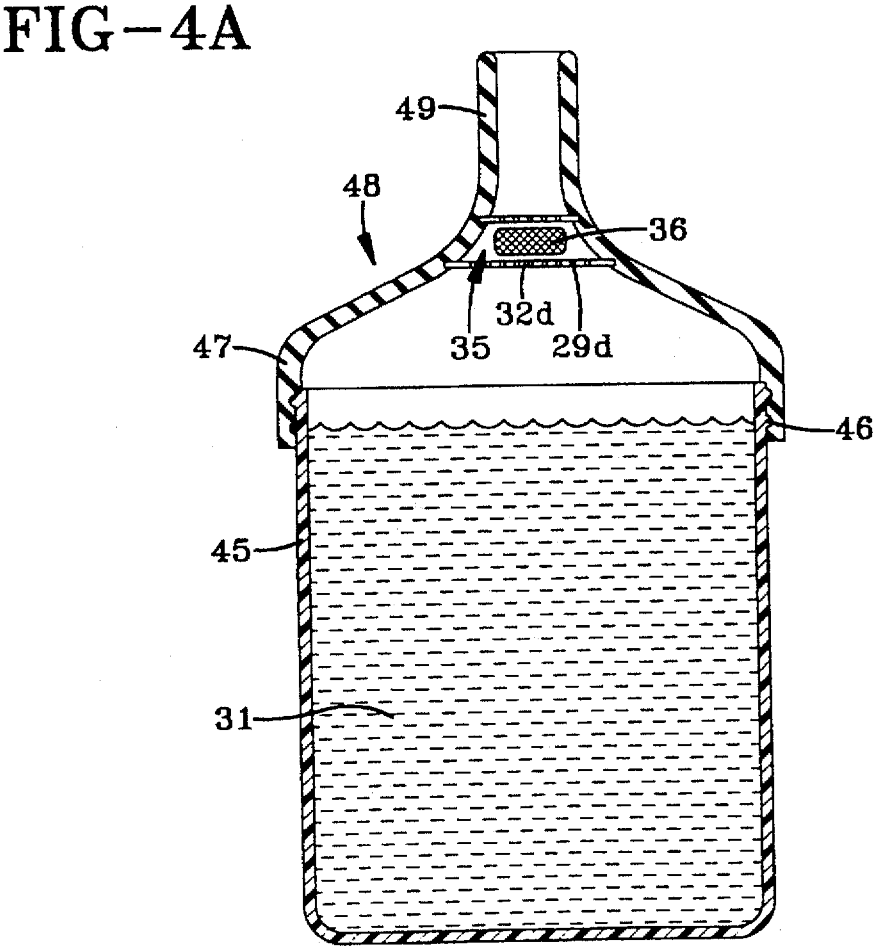
FIG. 4 is a view in section of an open-topped drinking glass or cup containing liquid for drinking with the top end embraced by the larger end of a funnel-shaped adapter, that may be used, for example, for a child's drinking cup, the support structure of the invention being mounted transversely across the neck or spout of the adapter, the support structure having a retention pocket formed of perforated plates between which is secured a beneficial agent.

Another form of the apparatus is seen in FIG. 4, which is a view in section of an open-topped drinking glass or cup 45 containing liquid for drinking 31 with the upper end 46 of the glass 45 embraced by the larger end 47 of a somewhat funnel-shaped adapter, indicated generally by the numeral 48, such as that usable for a child's drinking cup, the support structure 32*d* of the invention being mounted transversely across the neck or spout 49 of the adapter, the support structure 32*d* having a screen-like retention pocket 35 therein in which is secured at least one beneficial agent 34 and the support structure having perforations 29*d* formed therethrough. The support structure 32*a* may also be skeletal, if desired.

Figure 5A:
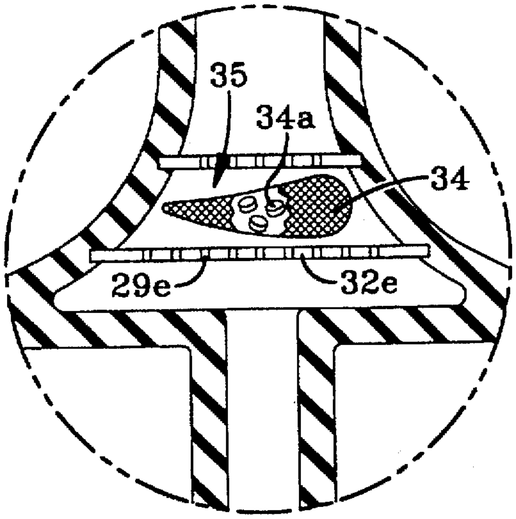
FIG. 5A is a greatly enlarged fragmentary view, partly broken away and in section, of the support structure and retention pocket shown in FIG. 5 and the beneficial agent dosage form held in a highly porous packet within the retention pocket.
Figure 5:
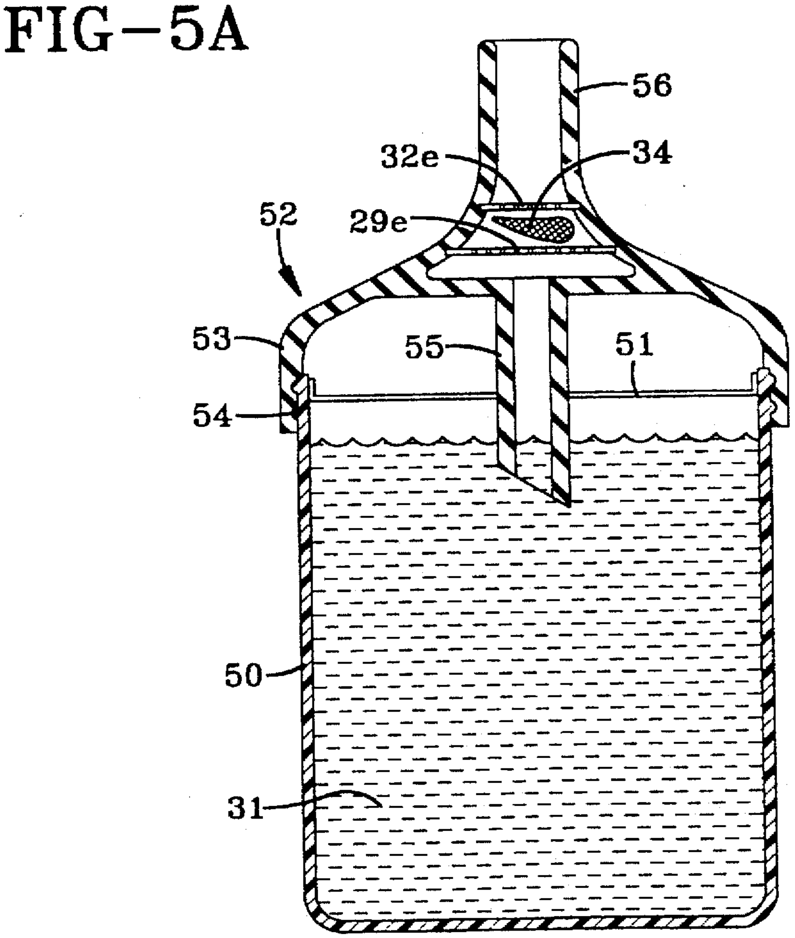
FIG. 5 is a view in section of a closed container containing a liquid for drinking with a pierceable substantially flat top, with a funnel-shaped adapter with the concave end of the funnel pressed over and around the top end of the container and with the support structure of the invention being mounted transversely across the neck or spout of the funnel-like adapter, the support structure having a retention pocket formed of perforated plates between which is secured a beneficial agent in particulate form in a highly porous envelope.

Another application of the present apparatus is shown in FIG. 5 in which there is seen a view in section of a closed container 50 containing a liquid for drinking 31 with a pierceable substantially flat top 51, such as that of a soft drink can or a vessel with a foil top, with a funnel-shaped adapter 52 with the concave end 53 of the adapter pressed over and around the upper end 54 of the container and a spike-shaped tube portion 55 mounted to the neck 56 of the adapter extending from the concave side of the adapter so as to pierce the top 51 of the container 50, and with the support structure 32*e* of the invention being mounted transversely across the neck or spout 56 of the funnel-like adapter 52, the support structure 32*e* having a retention pocket 35 formed of opposed plates having perforations 29*e* formed therethrough and between which plates there is secured a beneficial agent 34 in particulate form in a highly porous envelope 34*a* of the tea bag type.

Figure 6:
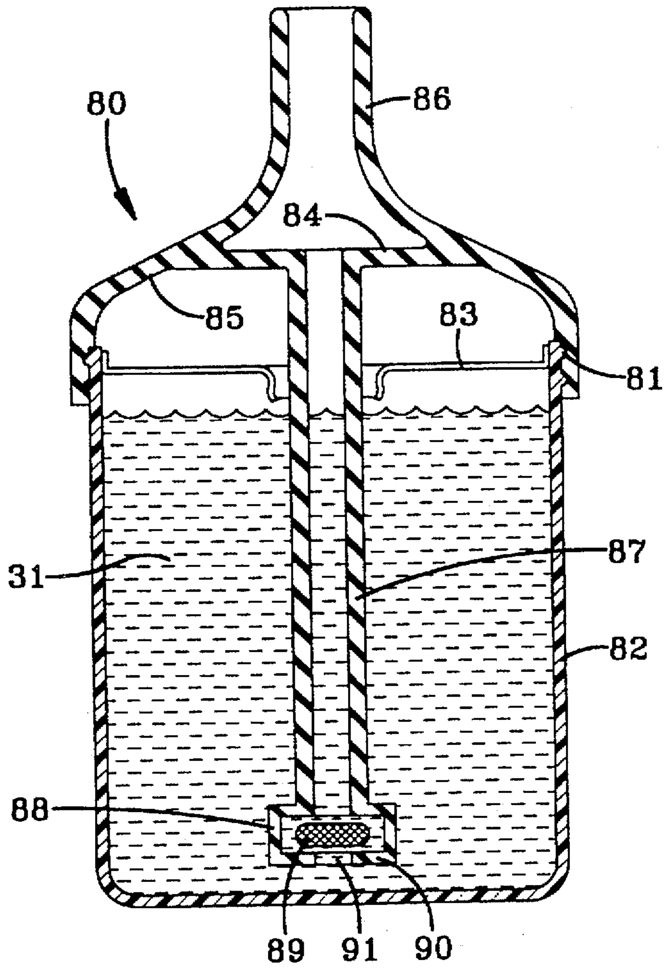
FIG. 6 is a view in section corresponding to FIG. 5 showing another embodiment of the support structure of the invention with a depending tube portion which is usable in a pierceable closed container such as a soft drink can or other container with a foil top.
Figure 7:
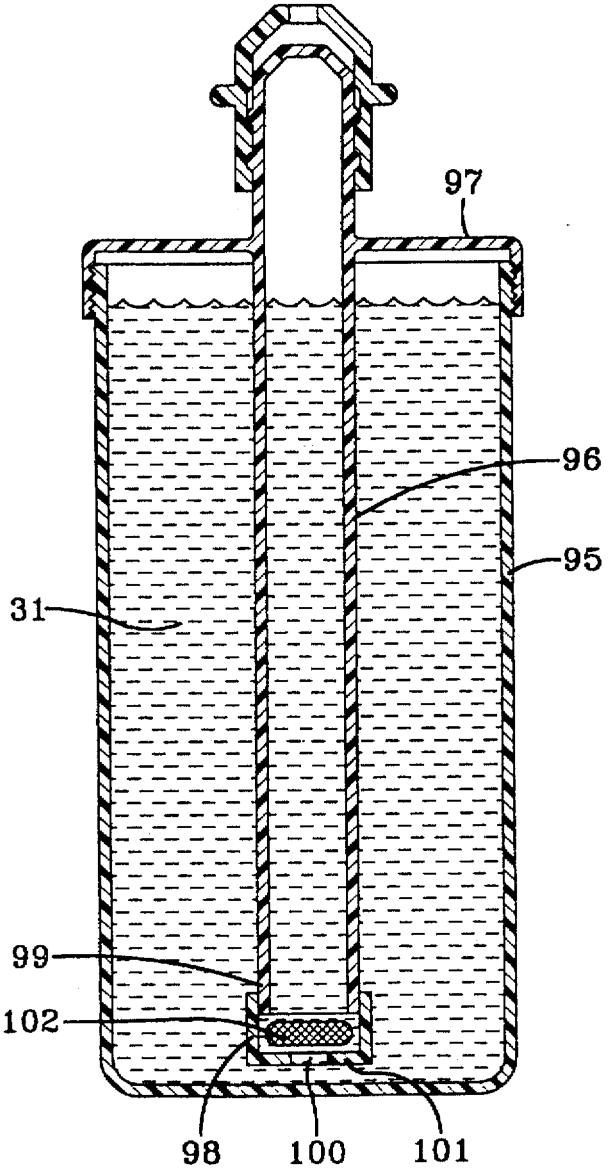
FIG. 7 is a view in section corresponding to FIG. 3 showing another embodiment of the support structure of the invention that is usable in a container such as a modified drinking bottle with a screw-on top with a reclosable cap.

If desired, the drinking tube concept may be extended as shown in FIGS. 6 and 7 in which the support structure securing the retention pocket is positioned at the bottom of the tube so that the beneficial agent therein (not shown) is not only drawn through the drinking tube, but can be immersed in the liquid just prior to oral administration thereof.

In FIG. 6 there is shown a container 82 filled with a liquid for drinking 31 and having the upper end 81 of the container enclosed by a funnel-shaped adapter 80. The concave underside 85 of the adapter 80 has transversely mounted thereacross a support member 84 from which projects downwardly a depending tube portion 87 that serves together with the neck or spout 86 of the adapter 80 as a drinking tube. The depending tube portion 87 has been thrust through a pierceable top 83 of the container 82. The pierceable top 83 is formed of a metal foil or thin plastic film that is readily pierced. At the lower end 90 of the depending tube portion 87 is affixed a transverse support structure 88 that encloses a retention pocket 89 in which is disposed at least one beneficial agent (not shown). A liquid inlet 91 on the underside 92 of the support structure 88 admits liquid for drinking 31 to the retention pocket 89 and up the depending tube 87.

This drinking tube concept is shown also in the drinking tube bottle 95 of FIG. 7 equipped according to the invention with a downwardly extending tube portion 96 that is integrally formed with a cover 97 that screws onto the top of the bottle 95. The downwardly extending tube portion 96 extends well into the liquid for drinking 31. A transverse support structure 98 is provided at the lower end 99 of the tube portion 96 where an inlet 103 on the lower side 101 of the support structure 98 admits liquid for drinking 31 through a retention pocket 102 held by the support structure. The retention pocket 102 holds one or more beneficial agents(not shown).

In all cases, it should be understood that those skilled in the art will understand how to add appropriate venting to the bottles or cans that may be desired to make withdrawal of liquid easier for the individual drinking therefrom.

Figure 8:
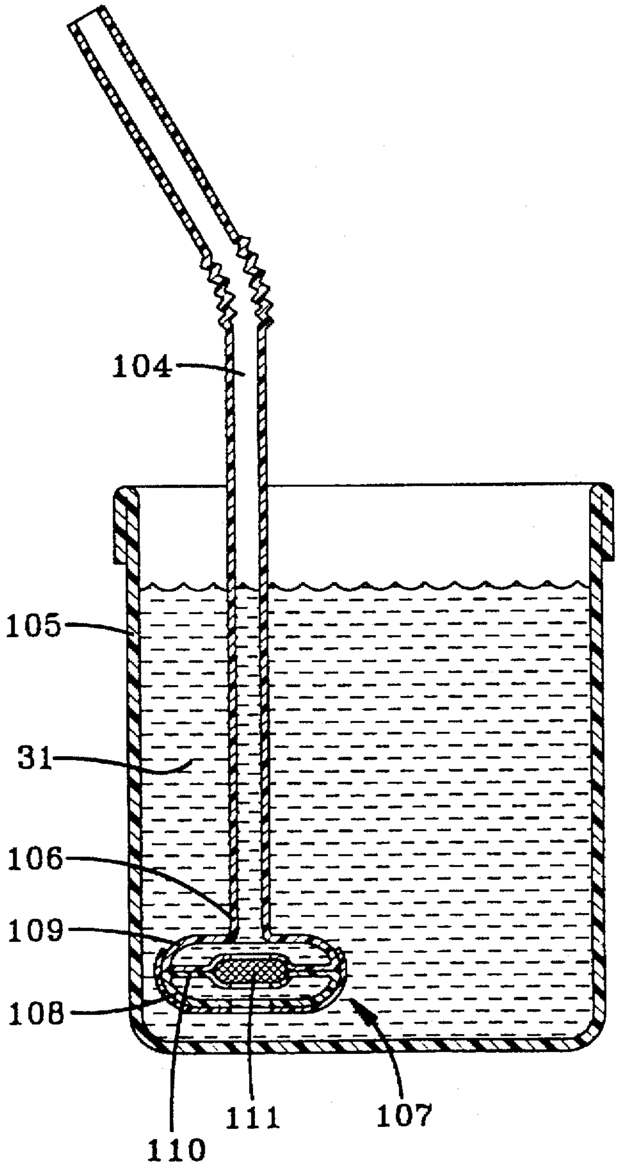
FIG. 8 is a view in section corresponding to FIG. 2 showing another embodiment of the support structure of the invention installed in a drinking tube used in an open top container.
Figure 9:
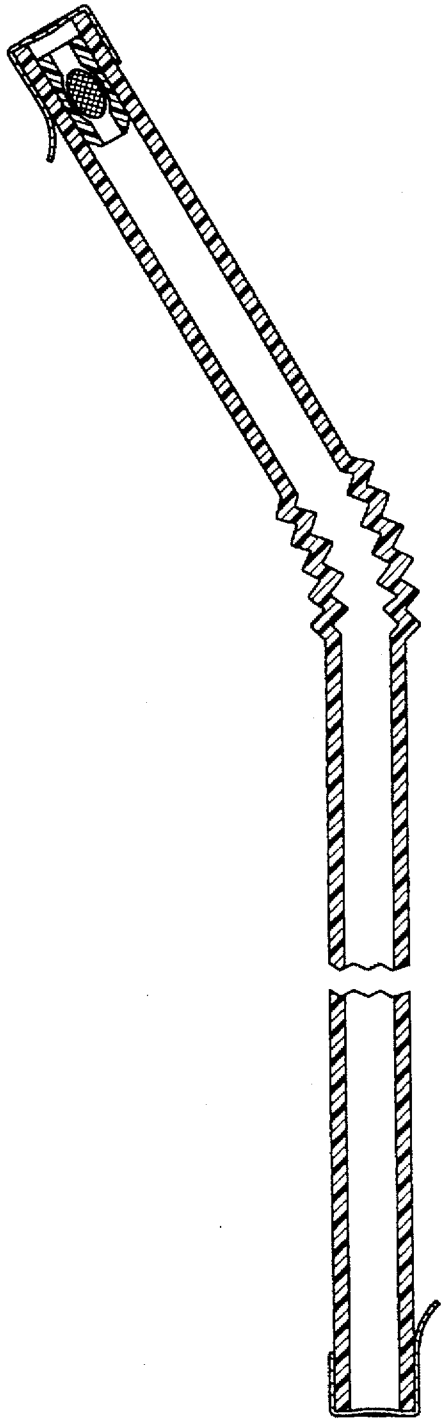
FIG. 9 is a view in longitudinal section of a drinking straw type tube having the support structure of the invention with a retention pocket therein simply wedged into a first end, the upper end, of the lumen of the drinking tube.
Figure 9A:
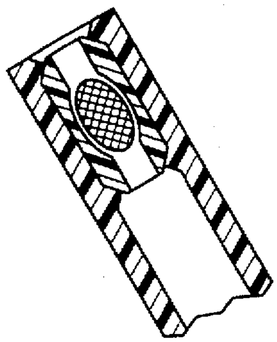
FIG. 9A is an enlarged fragmentary view in section of the upper end of a drinking tube such as shown in FIG. 9 with another embodiment of the support structure of the invention with a retention pocket therein that is held in the upper end of the drinking tube by a pair of resilient ridges formed on the inner wall of the drinking tube, one ridge at each end of the support structure.
Figure 10:
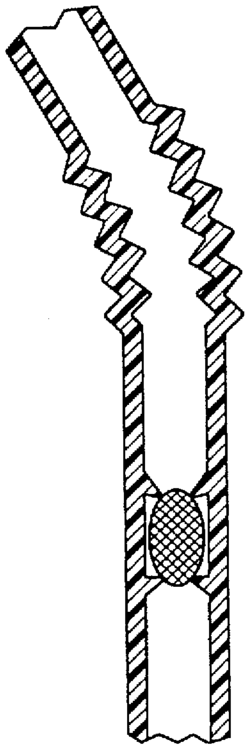
FIG. 10 is a fragmentary view in section of the middle part of a drinking tube with another embodiment of the support structure of the invention with a retention pocket therein installed in the drinking tube below the flexed mid-section and retained by a pair of inner annular ridges on the inner wall of the drinking tube.

A drinking tube 104 is shown in FIG. 8 inserted into an open top can or tumbler 105 filled with liquid for drinking 31. The drinking tube 104 is provided at its lower extremity 106 with an enlarged bulb portion 107 the lower half 108 of which is cemented or otherwise attached to the upper part 109 to enclose the transverse support structure 110 holding a retention pocket 111 with screen-like walls for holding beneficial agent(not shown).

The term liquid for drinking is to be understood for the purposes of the specification and claims to be most any liquid normally supplied to the individual to meet their needs in the way of a liquid diet or as a thirst quenching liquid or simply as a physiologically suitable liquid medium acceptable to the individual for the purpose of carrying one or more beneficial agents into the mouth for oral ingestion. Thus, the liquid for drinking includes infant formulas for infants and other nutritional formulas for older individuals entirely or partly dependent on a liquid diet, as well as beverages and water for thirst quenching or for the administration of medications or diagnostic agents or other beneficial agents.

Because there are often special needs for supplemental dietary factors, or other substances such as probiotics or electrolytes, or such substances admixed with flavoring agents to improve appetite or make a formula more palatable, as well as a need to administer medications or diagnostic agents, all these substances are understood to be beneficial agents that may be readily and simply provided to the individual, using the present apparatus and method, by addition to a liquid for drinking during oral administration, thereby beneficially modifying the liquid on an individual ad hoc basis.

The beneficial agents are utilized in controlled release form, or other protected dosage form in which the beneficial agent is stable and protected from moisture or deleterious airborne substances. Controlled release, as from an osmotic pump device, should be timed to deliver the beneficial agent during the time interval the individual will be drinking, for example, during a period of a few minutes to an hour or more. During the interval of drinking the amount of beneficial agent to be taken up by about 8 ounces of liquid for drinking will ordinarily be in the range of a few milligrams to not exceeding about 10 grams but more usually will be a quantity less than 5 grams per 8 ounces of liquid for drinking, and correspondingly less if a smaller quantity of liquid for drinking flows through the retention pocket of the support structure utilized.

Figure 11:
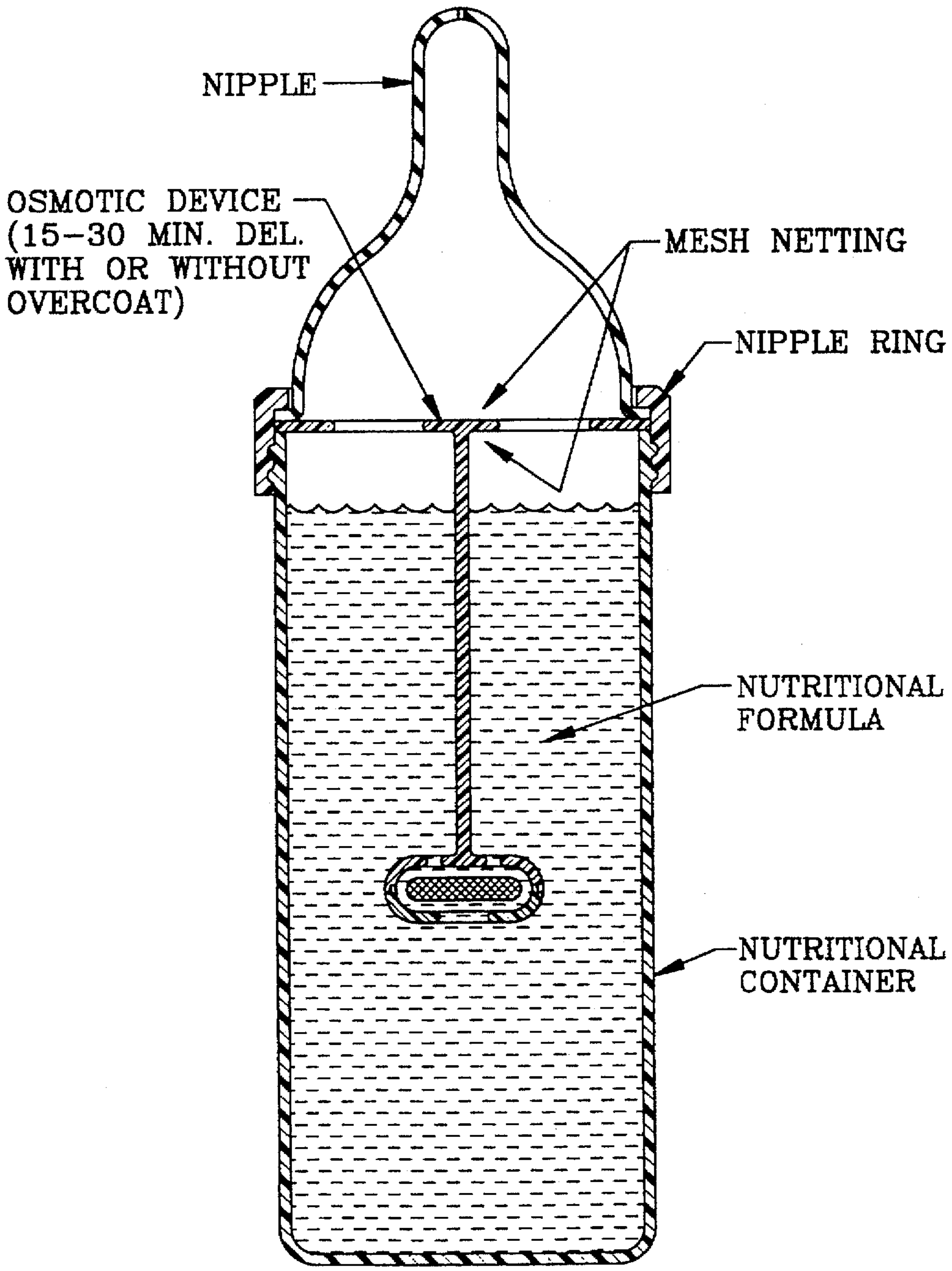
FIG. 11 is view in section of a nursing bottle similar to that shown in FIG. 1 but showing another embodiment of the support structure of the invention installed in a nursing bottle, the support structure suspending the retention pocket well down in the nursing bottle.
Figure 20:
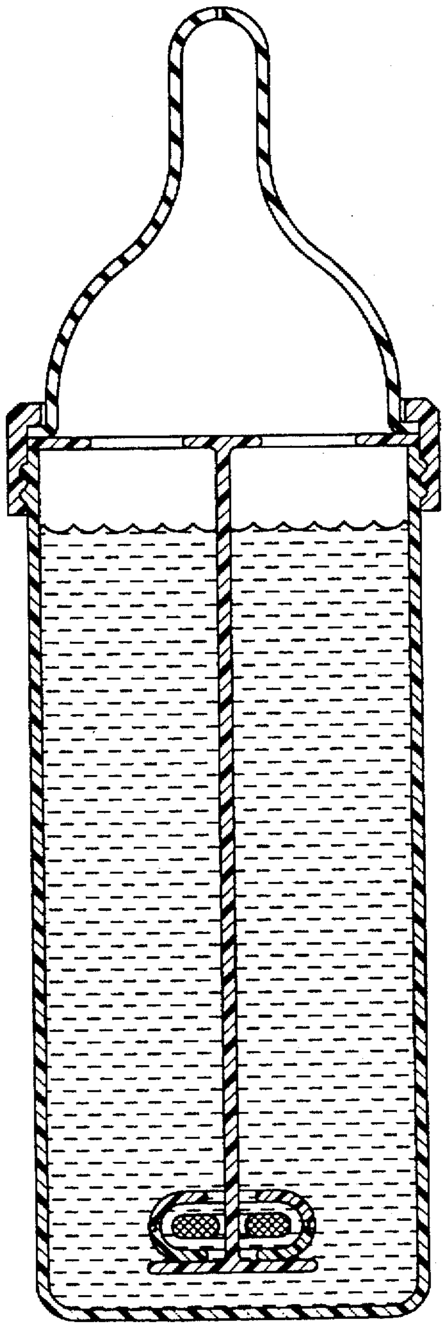
FIG. 20 is a view in section of a nursing bottle filled with a liquid for drinking similar to that seen in FIG. 11, with an embodiment of the support structure of the invention that includes a support rod that extends vertically well down into the liquid in the nursing bottle and carries slideably thereon a perforated retention pocket of somewhat toroidal shape shown resting on a disc at the lower end of the support rod, the retention pocket containing an envelope formed of screen and capable of holding a plurality of dosage forms of beneficial agent therein.

The support structure may be most any structure that holds a retention pocket for beneficial agent in the pathway of liquid for drinking, or, in the liquid for drinking for a sufficient time for the beneficial agent to be substantially taken up, i.e., dissolved or dispersed, in the liquid for drinking. For example, the retention pocket may be supported part way into a nursing bottle, as seen in FIG. 11, or the transverse support structure with retention pocket may be made slidable on a rod that depends from about the neck of the bottle as shown in FIG. 20, so that the retention pocket with beneficial agent is immersed when the bottle is upright, but moves to the top of the bottle when it is inverted as during nursing therefrom.

Figure 12:
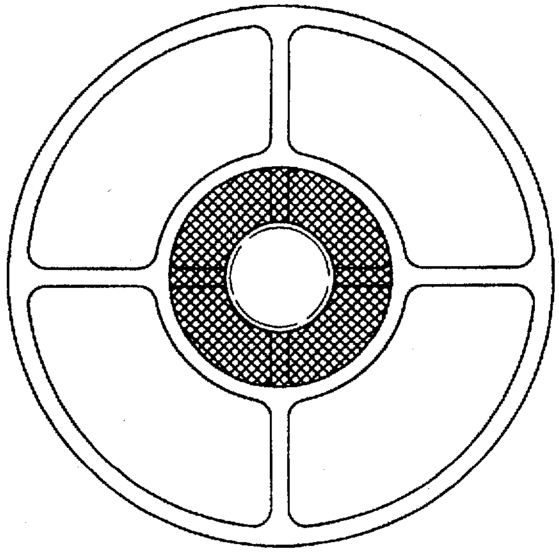
FIG. 12 is a top view of a suitable supporting structure for use in a nursing bottle with a wheel and hub-type skeletal structure supporting a retention pocket formed of a pair of opposing circular pieces of screen extending across the hub and with a beneficial agent in tablet form retained between the screens, the upper screen being omitted for purposes of illustration.
Figure 13:
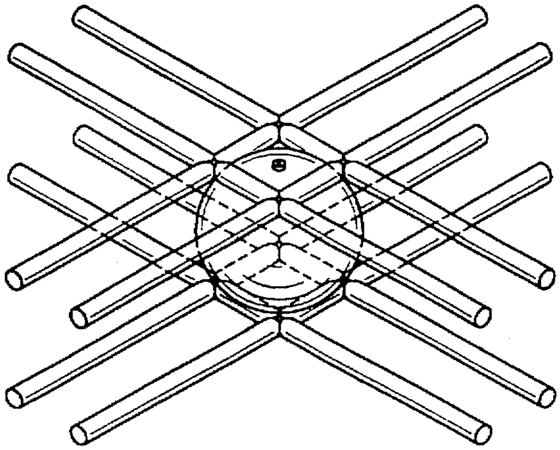
FIG. 13 is a perspective view section of a suitable skeletal supporting structure for use in a nursing bottle with a retention pocket formed of the skeletal cross support members and holding a beneficial agent in spherical tablet form.
Figure 21:
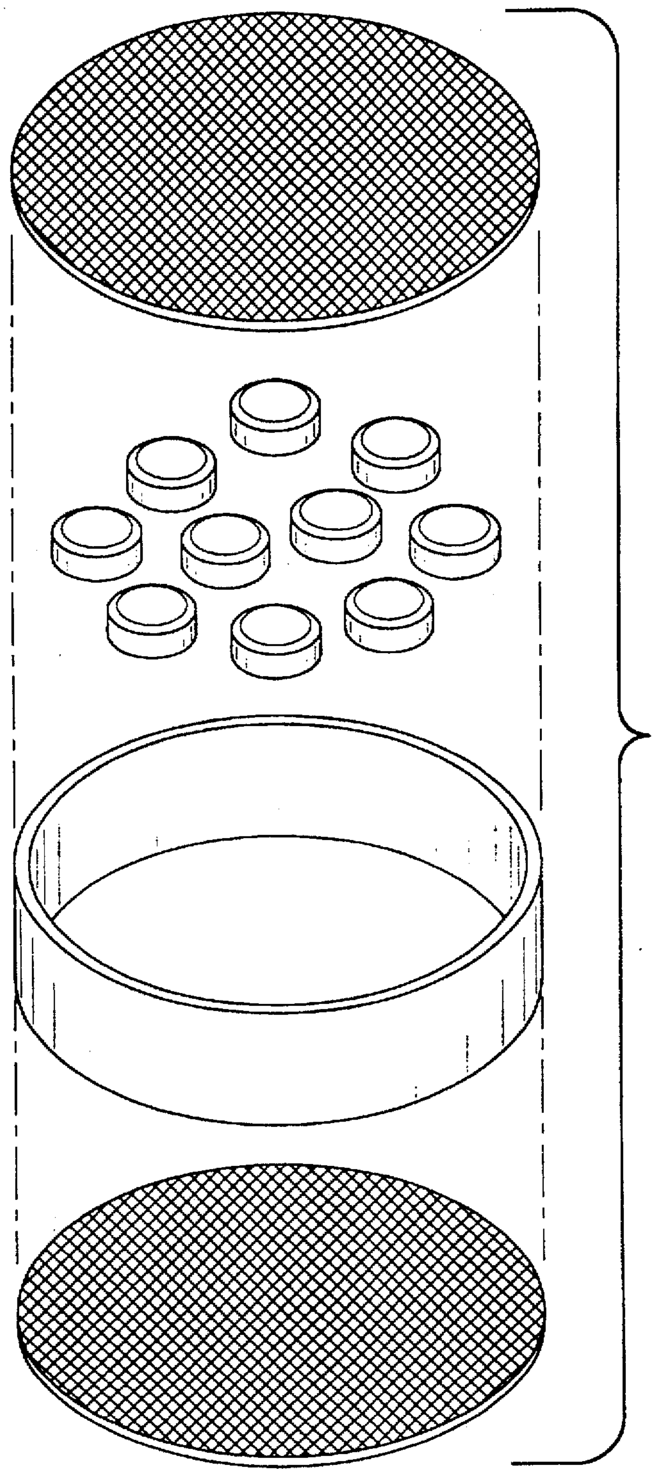
FIG. 21 is an exploded perspective view showing respective layers of a suitable supporting structure for use in a nursing bottle, the support structure being formed of a pair of face-to-face opposing circular screens with an intermediate circular annular spacer, the supporting structure also serving at the same time as a retention pocket and with a beneficial agent in tablet form retained between the screens.

The tablets or capsules or granules or particles of one or more beneficial agents may be retained in a retention pocket of various types, from the screen enclosures of FIGS. 12 and 21 to the skeletal structure of FIG. 13, which are merely illustrative. The tablets or osmotic devices that do not disintegrate may be held in skeletal structures, while the particulate materials and tablets that disintegrate should be retained in a screen or porous "tea bag" type retention pocket.

The support members are preferably made of an inert material that is suitable to use in contact with the liquid for drinking to be consumed, such as a non-corroding metal like stainless steel, or of a dimensionally stable inert plastic, such as a suitable polypropylene.

The beneficial agents are selected from the group consisting of nutrients, medicaments, probiotics, electrolytes, rehydration solutions and diagnostic agents that may be orally administered in the medium of a liquid for drinking having a viscosity in the range of about 1 to about 300 centipoises. Each at least one beneficial agent that is to be added in controlled release dosage form during feeding is added in at least a physiologically effective or diagnostically detectable amount.

A "physiologically significant" or "beneficial" ingredient is an ingredient that is, or is believed to be, nutritionally or pharmaceutically important to the patient, or is otherwise medically important as in the case of a probiotic, or, a diagnostic agent such as an opaquing agent.

A "probiotic" is understood to be a live or dead microbial food supplement which beneficially affects the human host by improving the individual's microbial balance in the gastrointestinal tract, e.g., *Lactobacillus reuteri* and *Lactobacillus acidolphilus.*

A "beneficial agent or ingredient that is dispersible in the medium of the liquid enteral nutritional product" is an agent or ingredient that is physiologically beneficially added, or otherwise usefully beneficially added, as in the case of a diagnostic agent, to the liquid for drinking during oral administration, and is dispersible in the medium of the liquid for drinking. The beneficial agents whether supplied in controlled release dosage form units or devices or non-controlled release dosage form and used according to the invention, must be dispersible in the medium of the liquid for drinking during an interval just prior to or during feeding, in order to meet the objectives of the invention.

A "useful amount" of a beneficial ingredient that is dispersible in the medium of the liquid enteral nutritional product is an amount that is "physiologically effective or diagnostically detectable" with respect to a patient, i.e., it produces, or is reasonably expected to produce, a detectable beneficial effect on the patient when orally administered. Generally not more than about 5 grams of beneficial agent will be contained in a single controlled release dosage form unit or device, and a plurality or even multiplicity of units such as microencapsulated microspheres containing a given beneficial agent may be employed to provide a desired level of the beneficial agent in the nutritional product being fed.

The phrase "at least one beneficial agent dispersible in the medium of the liquid for drinking" is meant to refer to the singular as well as the plural, as may well be adjudged from the context, and includes combinations of ingredients, agents or factors.

The term "dispersible" as used herein with respect to beneficial agent(s) is to be understood to apply to substances that are soluble as well as those that are suspendable enough to be taken up readily and carried along by the liquid medium of the liquid for drinking as that liquid flows through and around the retention pocket of the present apparatus, or as the retention pocket is immersed in the liquid for drinking just prior to its oral administration.

The "controlled release dosage forms" useful according to the invention are understood to include delayed or intermittent release as well as sustained release dosage forms, some of which constitute "rate controlling means" or "rate controlled dosage forms". Any dosage form that delivers, over a period of at least 30 minutes, a beneficial agent into a liquid for drinking, is considered to be a controlled release dosage form for the purposes of the invention. Preferably, the controlled release dosage forms prolong release of the contents thereof for a time appropriate to the nutrient or medicament being supplied.

The terms "controlled release dosage form units" or "controlled release dosage form particles" are to be understood to refer to individual coated tablets or coated capsules or devices such as osmotic delivery devices or microcapsule particles or small bundles of fine hollow fibers or small agglomerated clumps of molecular sieving type material, each capable of the sustained delivery or delayed or intermittent delivery of beneficial agent.

The controlled release dosage form unit will be preselected according to the contents thereof to provide the additional nutrient(s) and/or medicament(s) and/or flavoring agent(s) and/or probiotic(s) and/or diagnostic agent(s) and/or other beneficial ingredient(s) selected by the care giver in charge. As used herein and in the claims, medicaments are understood to be substances used in therapy.

The controlled release dosage form units employed will preferably be in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet.

Figure 14:
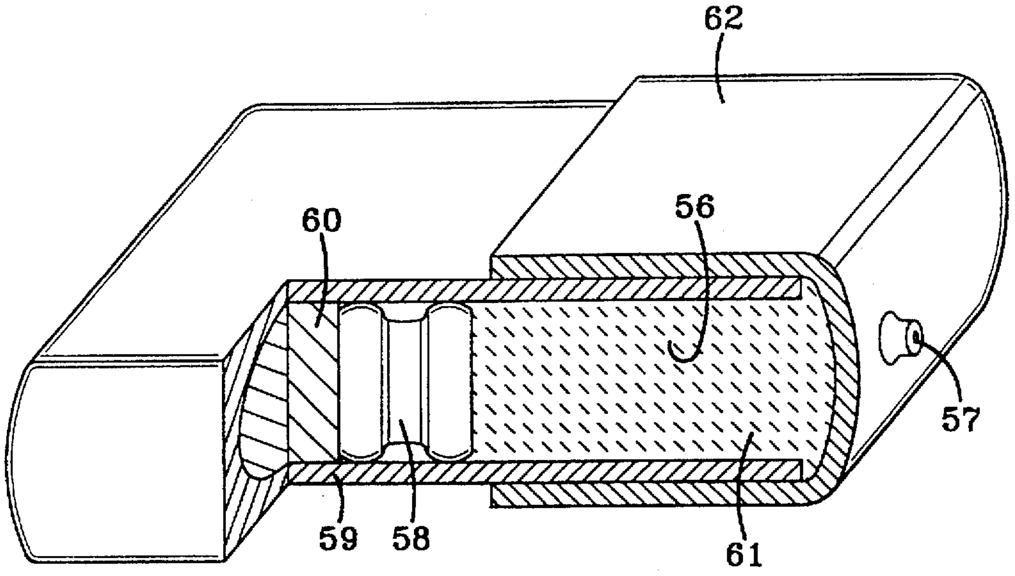
FIG. 14 is a perspective view, partly broken away and in section, of a rectangular solid-shaped sustained release reservoir, of the osmotic pump type, used to supply one or more beneficial agents within the retention pocket of the structure of the invention.

The controlled release dosage form unit depicted in FIG. 14 is of the osmotic pump type that functions in the manner of the osmotically driven delivery device described and claimed in U.S. Pat. No. 5,318,558, the specification and drawings of which are incorporated herein by reference with respect to the structure of the controlled release dosage form units therein described and the method of making them and their mode of functioning, albeit here with different environments and contents and end uses. In the pump type controlled release dosage form units, or delivery devices, the beneficial ingredient(s) in liquid form, i.e., either in the liquid state or in solution in a suitable solvent, is expressed out from a cylindrical enclosure or cavity 60 within the reservoir through a small orifice 57 by the action of a piston 58 driven by pressure developed by osmotic infusion of moisture through a semi-permeable membrane 59 confining a hydro-active substance **60*a* behind the piston 58, driving the piston steadily toward the side of the reservoir where the ingredient(s) 61 is forced out through the orifice 57. Orifice 57 is very small and is preferably drilled by a laser beam. The cylindrical enclosure 56 is formed within an outer non-permeable membrane or coating 62. The hydro-active substance 60*a*** may be a water-soluble salt like magnesium sulfate, magnesium chloride, potassium sulfate, sodium chloride, sorbitol, inositol, urea, or a saccharide such as glucose or fructose or dextran, or, a hydrophilic polymer such as a poly(hydroxyalkyl methacrylate) with a molecular weight of 30,000 to 5,000,000, or a poly(vinylpyrrolidine) with a molecular weight of 10,000 to 360,000, an anionic or cationic hydrogel or polyvinyl alcohol having low acetate residual.

Figure 15:
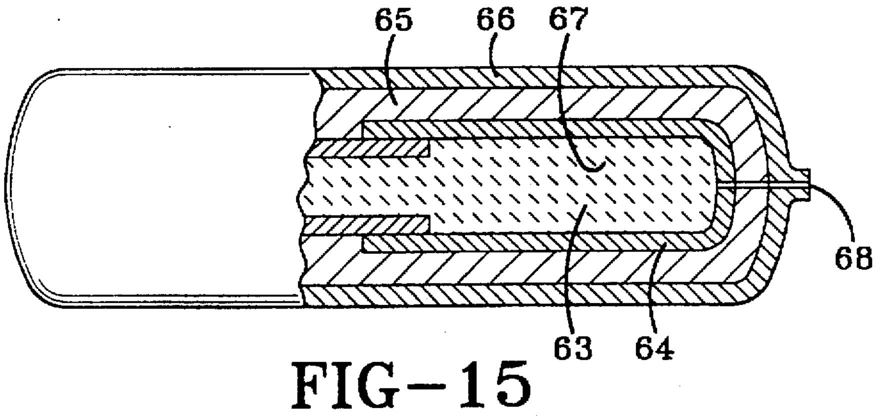
FIG. 15 is a view in front elevation, partly broken away and in section, of a nearly rectangular solid-shaped controlled release dosage form, of another osmotic device type, used to supply a beneficial agent or mixture of beneficial agents within the retention pocket of the support structure of the invention.

The controlled release reservoir depicted in FIG. 15 is another osmotic dosage system with a sustained release dosage form that functions in the manner of the osmotically operated delivery device described and claimed in U.S. Pat. No. 5,324,280, the specification and drawings of which are hereby incorporated herein by reference with respect to the structure of the sustained release dosage form units there described and the method of making them and their mode of functioning, albeit here with different environments and contents and end uses. In this type of system, the beneficial agent(s) 63 to be fed in liquid state or solution form, is enclosed within a non-permeable coating 64 that is surrounded by a layer 65 of hydro-active material that is entirely confined within an outer semi-permeable membrane coating 66. Osmotic pressure developing in the hydro-active layer 65 upon infusion of moisture thereinto compresses the core 67 containing the liquid form beneficial agent(s) 63 and forces that liquid out steadily through a very small passageway 68 from the core 67 to the exterior of the reservoir.

Figure 16:
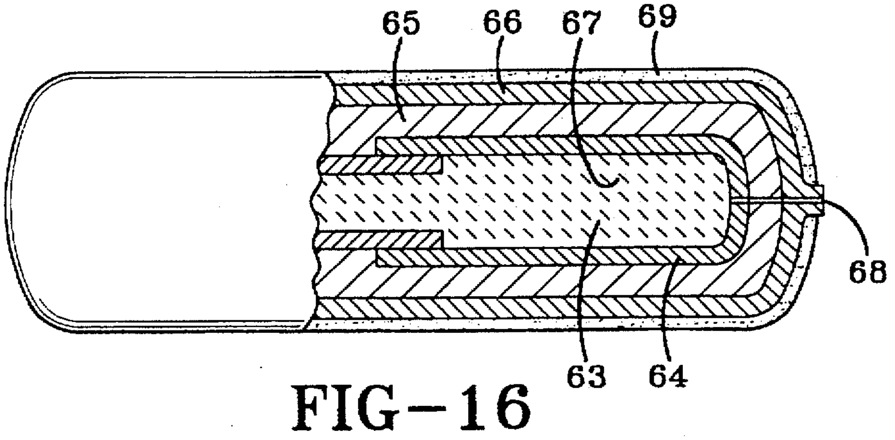
FIG. 16 is a view similar to FIG. 15 of a sustained release dosage form of the same type but with an external coating of a beneficial agent, such as a medicament, that is readily taken up immediately upon contact with the medium of a liquid for drinking while confined within a retention pocket of the support structure of the invention and brought into contact with a liquid for drinking.
Figure 17:
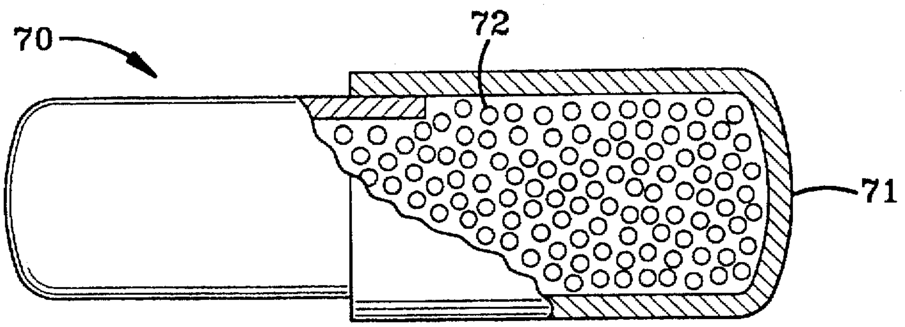
FIG. 17 is a view in front elevation, partly broken away and in section, of a nearly cylindrical solid-shaped carrier containing solid particles or granules of beneficial agent whether in controlled release dosage form or in non-controlled release form, used to supply a beneficial agent or mixture of beneficial agents within the retention pocket of the support structure according to the invention.

Turning now to FIG. 16, the controlled release dosage form unit as shown in either of FIGS. 14 and 15 may be coated with a readily soluble coating, such as coating 69 of a beneficial agent, such as a medicament, for the purpose of getting a quick initial release of such beneficial agent. This may be desirable in order to get a blood content level up quickly, after which a steady sustained release level may be needed.

The controlled release reservoir 70 depicted in FIG. 16 is of the type in which there is provided, within a carrier envelope 71 that is very quickly soluble or disintegrable in the medium of the liquid enteral nutritional product, a quantity of microcapsules or molecular sieving type particles 72. If microcapsules, the particles 72 are microspheres each individually coated and each containing the same beneficial agent or mixture thereof, with a plurality of distinct numerical portions or fractions thereof each provided with a coating that dissolves or disintegrates in or is permeated by the medium of the liquid enteral nutritional product. The various numerical fractions, respectively, each have a coating of a different thickness whereby upon making a blend of the microcapsules with a fraction that is uncoated, the mixture shows a sustained release effect when exposed to an aqueous medium. The envelope and coatings must essentially be acceptable for oral administration, i.e., suspendable, but not necessarily soluble.

If the particles 72 are of a molecular sieving type, or a mixture of two or more molecular sieving grades, the particles have been impregnated with one or more beneficial agents to be supplied during administration and the particles agglomerated into desired size granules or clumps that are usable with or without being coated, to form a controlled release dosage form usable according to the invention, the coating, if applied, being soluble, or disintegrable, i.e., suspendable, in or permeable to the medium of the liquid for drinking. The molecular sieving type material has a porous structure with non-aligned pores where pore size is critically controlled in manufacture in order to create the property of holding molecules of different size characteristics or molecular weights in a selective manner. The holding or storing properties impart sustained release behavior.

The carrier for controlled release dosage form units may also take the form shown in FIG. 16 but containing a fibrous material in which the fibers are hollow and permeable and slowly release substances such as the beneficial agents herein added to a liquid for drinking. A measured quantity of such fibers, in a coil or in chopped form, may be used in a retaining means such as a sleeve or bag, or agglomerated with a binder, or coated with a dispersible, disintegrable or permeable coating or simply placed in a retention pocket. Such fibers, which may be formed primarily of a cellulose ether or ester, are capable of storing up and subsequently yielding up a beneficial ingredient or mixture of ingredients, upon contact with flowing liquid for drinking during oral administration.

Figure 18:
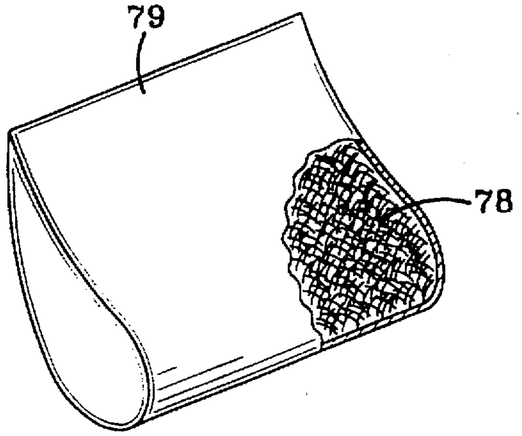
FIG. 18 is a perspective view, partly broken away and in section, of a highly permeable fibrous packet, preferably of the non-woven tea bag-type of carrier, suitable for placing in a retention pocket of the support structure according to the invention, and capable of holding a plurality of particles or granules of one or more beneficial agents, in sustained release dosage form or non-controlled release dosage form, including microencapsulated particles or molecular sieving type material or permeable hollow fibers, each such dosage form particle or unit containing at least one beneficial agent.
Figure 19:
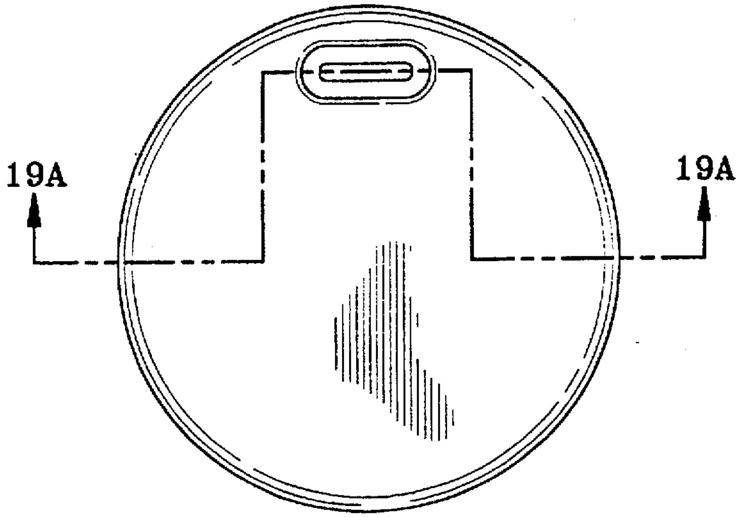
FIG. 19 is a top view of an open top container such as a child's cup or tumbler with a somewhat funnel-shaped adapter pressed over the top end of the container, the adapter having a drinking spout extending upwardly from near an edge of the adapter, and thus, near a side of the cup.
Figure 19A:
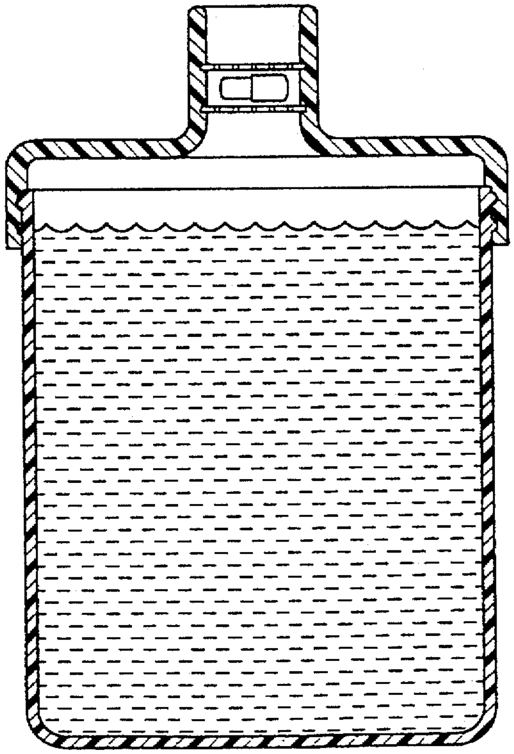
FIG. 19A is a view in section, taken along dog-legged line 19A—19A of FIG. 19, of an open top container containing liquid for drinking and with the top end embraced by the larger end of the somewhat funnel-shaped adapter, such as that used for a child's drinking cup, the support structure of the invention being mounted transversely across the neck or spout of the adapter, the support structure having opposed perforated plates forming a retention pocket in which is secured a beneficial agent.

The fibrous and highly porous tea bag-type of carrier envelope 79 shown in FIG. 18 may also be used to hold or support, within a retention pocket, a quantity of microencapsulated microspheres, or a quantity of molecular sieving type material or, for example, a quantity of chopped fine hollow permeable fibers 78, any of which forms may hold or contain a dosage amount of one or more beneficial agents. Such a tea bag-type of envelope, or a plurality thereof, may also be used to position within a formulation chamber any combination of: (1) one or more beneficial agents in controlled release dosage form; (2) one or more beneficial agents in controlled dosage form along with one or more beneficial agents not in controlled dosage form, wherein the beneficial agents not in controlled dosage form may be the same or different agents than those present in controlled dosage form; and (3) a flavoring agent in combination with either (1) or (2) and in a controlled release dosage form setting, as well as in any external coatings of controlled release dosage form units.

Any mode of making a sustained or controlled release storage coating, envelope or binder may be used in making a controlled release dosage form unit usable according to the invention so long as the soluble, dispersible or disintegrable components of the dosage form units used are physiologically acceptable and the controlled release dosage form unit is capable of storing one or more beneficial agents as above defined until use and releasing the same into a liquid for drinking at a useful rate or manner and/or over a useful period of time of at least a minute and up to about an hour during oral administration. Tablets and capsules and other dosage forms may generally be coated, if desired, for example for purposes of protecting beneficial agents from moisture and atmospheric gases prior to use, with well known materials that may slow down and delay the solubilization or suspension of the beneficial agent, materials such as zein, shellac, methacrylate polymers and copolymers, and cellulose ethers and esters that are frequently used for the purpose. Such materials are described in U.S. Pat. No. 5,160,742 and are generally adaptable for the present purpose, although the coated articles described in the patent are used in a different manner.

Wherein it is necessary or quite important to provide a beneficial agent, or a mixture of agents, as herein defined, for example, one or more medicaments, according to the invention and at a fairly uniform rate over time, with preferably not more than about a 25% variation above or below the median rate over a period of a few minutes to about an hour or more, the osmotic pump and other osmotic delivery systems are to be preferred.

Amongst the beneficial agents that are most likely to be added to a liquid for drinking that is a nutritional product are, for example, nutrients, such as, glutamine, arginine, fermentable dietary fibers, fermentable and non-fermentable dietary fibers, enzymes, phytochemicals, anti-oxidants, minerals such as traces of selenium, chromium, molybdenum, zinc, and copper, electrolytes, combinations of amino acids, oligosaccharides such as fructo-oligosaccharides, short chain ($C_3$–$C_4$) fatty acids, pyruvate precursors in the form of pyruvamide, or pyruvyl-amino acids, such as, pyruvyl-glycine, pyruvyl-alanine, pyruvyl-leucine, pyruvyl-valine, pyruvyl-sarcosamine and their amides, esters and salts, structured lipids, d-chiroinositol, lactoferrin, marine oils and ascorbic acid. An example of a structured lipid which provides excellent nutritional support is a glycerol backbone with at least one gamma linolenic acid or dihomogamma-linolenic acid residue in combination with a medium chain ($C_6$–$C_{12}$) fatty acid residue and a $C_8$–$C_{22}$ n-3 fatty acid residue selected from alpha-linolenic and stearodonic, eicosapentaenoic and docosahexaenoic acid.

A rehydration solution is used for treatment of mild to moderate dehydration, correcting volume depletion and replacing fluids and electrolytes lost during conditions such as diarrhea and vomiting.

Phytochemicals include broccoli extracts, carotenoids, iso-flavones and iso-flavenoids.

Medicaments that may usefully be administered in this manner include, for example, antihistamine drugs; anti-infective agents, such as antibiotics, antivirals and urinary tract anti-infectives; antineoplastic agents; autonomic drugs such as adrenergic agents and skeletal muscle relaxants; blood formation and coagulation drugs; cardiovascular drugs; central nervous system agents; diagnostic agents; electrolytic, caloric and water balance agents; enzymes; antitussive, expectorant and mucolytic agents; gastrointestinal drugs such as antacids; gold compounds; hormones and synthetic substitutes; smooth muscle relaxants; and unclassified therapeutic agents. Other examples are $H_2$ blockers like Tagamet®, prokinetic medications, bioactive peptides, medication for diabetic condition, chemotherapy agents, or any medication intended for oral administration that will not react adversely with a nutritional product being fed.

Flavoring agents that may be usefully administered in this manner include natural and synthetic flavors and flavor enhancing substances.

Probiotics that may be usefully administered in this manner include, for example, *Lactobacillus acidophilus* GG, as described in U.S. Pat. No. 4,839,281, *Lactobacillus reuteri*, *Lactobacillus animalis*, and *Lactobacillus salivarius*, as described in WO 93/02558. Probiotics are live or dead microorganisms that aid in the digestion of food or that help control the population of harmful microorganisms in the intestines.

Diagnostic agents that may be usefully administered in this manner include opaquing materials.

Electrolytes that may be usefully administered in this fashion include physiologically acceptable sodium and potassium salts and chloride salts.

Among the advantages of the invention are the relative ease and low cost of making up a tailor-made modified diet for an individual on a liquid diet to meet special or temporary needs, as well as the ability to administer many medications orally instead of by injection. It is also of advantage to be able to administer beneficial agents that are not stable in pre-prepared liquid diets, but are available in dissolvable or disintegrable tablets or capsules in which the beneficial agent is stable.

We claim:

1. An apparatus for adding a useful amount of at least one beneficial agent to a liquid, said apparatus comprising:

a spout structure, said spout structure constructed to be mounted on a container containing a liquid, said spout structure defining an outlet port, said outlet port being the sole outlet through which a liquid contained in the container can exit the container to which said spout structure is mounted, said spout structure defining a first liquid flow path therethrough;

a support structure extending transversely of said first liquid flow path defined by said spout structure, said support structure defining a retention pocket having liquid penetrable walls, said support structure defining a second liquid flow path through said liquid penetrable walls and through said retention pocket, said first and second liquid flow paths in fluid communication with one another;

and at least one beneficial agent secured by said retention pocket in fluid communication with said second liquid flow path, said at least one beneficial agent comprising a probiotic; and said at least one beneficial agent being in a form adapted to be taken up in a liquid.

2. The apparatus of claim 1 in which the at least one beneficial agent is in the form of a granulated solid.

3. The apparatus of claim 1 in which the at least one beneficial agent is in the form of a dissolvable tablet.

4. The apparatus of claim 1 in which said at least one beneficial agent is contained in an osmotic device.

5. The apparatus of claim 1 in which said at least one beneficial agent is contained in controlled release form in a molecular sieving structure.

6. The apparatus of claim 1 in which said at least one beneficial agent further comprise a beneficial agent selected from a group consisting of: nutrients, medicaments, electrolytes, rehydration solutions, diagnostic agents, and combinations thereof.

7. The apparatus of claim 1 in which said spout structure comprises a drinking straw.

8. The apparatus of claim 1 in which said at least one beneficial agent further comprises a beneficial agent selected from a group consisting of: glutamine, hydrolysates, amino acids, polyamines, pyruvates, proteins, carbohydrates, oligosaccharides, phytochemicals, soluble fibers, lactoferrin, marine oils, structured lipids, fats, vitamins, minerals, and combinations thereof.

9. The apparatus of claim 1 in which a flavoring agent is positioned along with the at least one beneficial agent.

10. A method of modifying a liquid comprising the steps of:

providing a liquid in a vessel from which the liquid is to be administered;

providing a spout structure, said spout structure constructed to be mounted on said vessel, said spout structure defining an outlet port, said outlet port being the sole outlet through which said liquid can exit said vessel when said spout structure is mounted on said vessel, said spout structure defining a first liquid flow path therethrough, said spout structure comprising a support structure extending transversely of said first liquid flow path defined by said spout structure, said support structure defining a retention pocket having liquid penetrable walls, said support structure defining a second liquid flow path through said liquid penetrable walls and through said retention pocket, said first and second liquid flow paths in fluid communication with one another, at least one beneficial agent secured in said retention pocket in fluid communication with said second liquid flow path, said at least one beneficial agent comprising a probiotic;

placing said spout structure on said vessel such that said outlet port is the sole outlet through which said liquid can exit said vessel; and passing said liquid through said first and second liquid flow paths and through said outlet port.

11. The method of claim 10 in which a flavoring agent is provided in the retention pocket in addition to the at least one beneficial agent.

12. The method of claim 10 wherein said spout structure comprises a drinking straw.

* * * * *

UNITED STATES PATENT AND TRADEMARK OFFICE

CERTIFICATE OF CORRECTION

PATENT NO. : 5,707,353
DATED : January 13, 1998
INVENTOR(S) : Mazer et al.

It is certified that error appears in the above-identified patent and that said Letters Patent is hereby corrected as shown below:

Column 14, line 64, change "comprise" to --comprises--.

Signed and Sealed this

Twenty-third Day of June, 1998

Attest:

Bruce Lehman

BRUCE LEHMAN

*Attesting Officer*

*Commissioner of Patents and Trademarks*